United States Patent [19]
McClintock et al.

[11] Patent Number: 5,980,828
[45] Date of Patent: Nov. 9, 1999

[54] COMBINED SAMPLING-ASSAY DEVICE AND HOLDER

[75] Inventors: Joseph A. McClintock, Baltimore; Afzal Chowdhury, Columbia; Mary Ann Childs, Baltimore; Gregory K. Shipman, Catonsville; David Bernstein, Eldersburg; Uri Reichman, Baltimore; Craig A. Chung, Gaithersburg, all of Md.

[73] Assignee: Universal Healthwatch, Inc., Columbia, Md.

[21] Appl. No.: 08/864,377

[22] Filed: May 28, 1997

Related U.S. Application Data

[60] Provisional application No. 60/018,512, May 28, 1996.
[51] Int. Cl.$^6$ .................................................... G01N 33/48
[52] U.S. Cl. ............................. 422/58; 422/61; 422/100
[58] Field of Search .......................... 422/56, 58, 61, 422/100, 102

[56] References Cited

U.S. PATENT DOCUMENTS

| | | | |
|---|---|---|---|
| 4,259,964 | 4/1981 | Levine | 422/61 |
| 4,385,113 | 5/1983 | Chappelle et al. | 435/8 |
| 4,396,579 | 8/1983 | Schroeder et al. | 422/52 |
| 4,559,949 | 12/1985 | Levine | 422/61 |
| 4,826,759 | 5/1989 | Guire et al. | 422/61 |
| 5,308,580 | 5/1994 | Clark | 422/61 |
| 5,366,867 | 11/1994 | Kawakami et al. | 435/8 |

OTHER PUBLICATIONS

DeLuca et al., "Factors Affecting the Kinetics of Light Emission from Crude and Purified Firefly Luciferase", Anal. Biochem., 95:194–198 (1979).

*Primary Examiner*—Lyle A. Alexander
*Attorney, Agent, or Firm*—Foley & Lardner

[57] ABSTRACT

A combined sample-assay device allows sampling and detection within an integrated device. The device is a flat plate-like body with a collection arm. The collection arm optionally folds to enter a recess that flatly supports and seats the arm. The arm may be friction held in this recess and completely enters the recess. Within the recess is a second recess that contains a reading portion and transport portion. Chemiluminescent or other light emitting chemical reagent is placed within the device and light is detected in response to the presence of a sample analyte in a fluid sample.

13 Claims, 1 Drawing Sheet

COMBINED SAMPLING-ASSAY DEVICE AND HOLDER

This application claims the benifit of U.S. Provisional Application Ser. No. 60/018,512, filed May 28, 1996

BACKGROUND

The ability to detect bacterial contamination is paramount to improving food safety. During food processing, food can become contaminated with bacteria and spoil. Food poisoning can result if food contaminated with pathogenic bacteria, or its toxic products, is ingested without proper cooking.

Standard culture plate methods for monitoring surfaces for bacterial contamination require a sterile sample collection device (generally a swab or sponge) and suitable culture media, which after inoculation, must be incubated at a controlled temperature for a minimum of several hours to days. These methods are too cumbersome and time consuming, especially if used by untrained workers. Rapid bacteria tests need to be implemented in slaughterhouses and food handling establishments to improve safety. In these establishments, one must rapidly determine whether additional cleaning is required or whether proper safety procedures have been followed. To do that, a quick, reliable bacteria measurement is needed. Unfortunately, this is often not possible because present methods require several hours or even days by trained laboratory technicians or require elaborate testing equipments that are not readily transportable to on site locations.

Attempts have been made to overcome these shortcomings with more sensitive chemiluminescence detection methods. One such chemiluminescence method measures adenosine triphosphate (ATP) to indirectly measure the bacteria content. This detection is reliable because all bacteria contain some ATP. Chemical bond energy from ATP is utilized in the chemiluminescent reaction occurring, for example, in the tails of the firefly *Photinus pyralis*. The mechanism of this chemiluminescence reaction has been well characterized (DeLuca, M., et al, 1979 Anal. Biochem. 95:194–198). The components of this reaction can be isolated free of ATP and subsequently used to detect ATP in other sources by a reaction that begins with formation of an enzyme bound luciferyl-adenylate complex and free inorganic pyrophosphate and ends with a rapid reaction of this complex with molecular oxygen to produce light, $CO_2$, and adenosine monophosphate (AMP).

One conventional light measuring method involves counting photons with a light measuring instrument. Photographic films also have been used to monitor chemiluminescent reactions, as described for example in U.S. Pat. No. 4,396,579. A drawback of these types are that they are complex and difficult to use.

Firefly luciferin-luciferase reactions have been used for detecting microorganisms, as described in U.S. Pat. Nos. 4,385,113 and 5,366,867. These methods, however, suffer a number of deficiencies. Lyophilized luciferase-luciferin reagent is unstable at room temperature during long term storage and is unstable after liquid reconstitution over short time intervals. Additionally, after reconstitution, the reagent solution emits significant amount of light even in the absence of ATP, which decreases detection sensitivity.

The reagent instability problem was partly addressed by drying luciferin-luciferase reagents separately onto plastic surfaces. But this required an additional step of transferring microorganisms from a collection device to a plastic surface, increasing complexity. Further, while this solves the instability problem, it unfortunately lowers the detection sensitivity and creates a new problem—incomplete ATP transfer from the collection device to a separate plastic surface containing the luciferase-luciferin reagent. Furthermore, this solution introduces a new time variable between the transfer and the light emission measurement.

Adding reagent at timed intervals causes additional problems because the light emission kinetics become shorter as the light intensity decreases. The twin timing and reagent instability problems also plague other so chemiluminescence chemistries that have been developed to detect target analytes. For example, U.S. Pat. No. 4,396,579 describes a complicated, expensive automated machine designed to add chemiluminescent reagent at fixed time intervals to overcome the light emission kinetic problem. The reagent instability and the timing problems make this machine unusually complex.

Thus, there is a need for an assay device that benefits from high sensitivity and speed of chemiluminescence detection, but one that excludes the aforementioned complexity, timing, reagent instability, and high background light emission problems. Copending U.S. patent application Ser. No. 08/560,094, filed Nov. 17, 1995 (hereafter "first copending application"), entitled CHEMILUMINESCENT ASSAY METHODS AND DEVICES FOR DETECTING TARGET ANALYTES, describes chemiluminescent assay methods and devices that fulfill this need. The disclosure of the first copending application, including its drawings, is incorporated herein by reference.

The first copending application discloses a simple, easy to use chemiluminescent sampling assay device that eliminates or reduces the complexity associated with manually measuring and adding reagent at timed intervals. This sampling device also provides means to measure light intensity and allows rapid analysis of target analytes at the sample site. Specifically, it comprises a container or envelope holding a sampling strip having separate sampling and reagent portions. The reagent portion contains one or more dried chemiluminescent reagents. The device has a light-permeable portion that permits light generated by a chemiluminescent reaction within the sampling strip to exit the container. This sampling assay device eliminates or reduces much of the complexity associated with other known assay methods and, as a result, decreases the cost and training requirements for detecting target analytes. A wide range of target analytes can be detected by this device. In fact, the sampling portion of the device can collect virtually any type of target analyte containing ATP, not only from physical contact with a solid, but also from sample liquid applied or introduced thereto. The advantage of rapid and sensitive detection of bacteria can be realized through sensitive light detection using, for example, a photomultiplier. The first copending application discloses, in essence, a compact, self-contained assay device that allows light detection using any of known light detection methods, including an optical observation.

Notwithstanding the advantages and benefits of the ATP detection method described in the first copending application, the ATP detection method tests for presence of microorganisms, not a specific microorganism, since all microorganisms contain ATP. In this regard, it would be desirable to detect specific microorganisms.

Conventional instruments for measuring chemiluminescence, including luminometers and fluorometers, however, are not particularly suited for such an assay device that has a flat geometry. To this end, there is a need for a portable interface readily interfaceable with a photomultiplier or other known light detector to provide a simple, efficient light intensity reading from the sampling assay device of the type disclosed in the first copending application. Copending U.S. patent application Ser. No. 08/577,107, filed Dec. 22, 1995 (hereafter "second copending application"), entitled SAMPLING-ASSAY INTERFACE SYSTEM AND METHOD describes a system that fulfills this need, the disclosure of which, including its drawings, is incorporated herein by reference.

Specifically, the second copending application describes a sampling-device holder interface system and a method for performing an assay for a target analyte from a sampling device of the type disclosed in the first copending application. The sampling system includes a sampling-device holder interface (hereafter "interface") and a quantifier for converting the output signal to quantifiable data indicative of the amount of the target analytes. Specifically, the interface comprises a sampling-device holder and a light detector—means for converting light generated from the sampling device to an output signal corresponding to the amount or intensity of the light generated—such as a photomultiplier or photodetector.

The interface holds a sampling device, which comprises a container and a sampling strip inside the container. The sampling strip has a sampling portion for introducing a sample, a reading portion containing a reagent for producing a chemiluminescent reaction with the target analytes, and a transfer portion connecting the sampling and reading portions for transferring the sample from the sampling portion to the reading portion. The container has an opening to permit introduction of samples to the sampling portion. It also has a light transmissive portion, such as a window or opening, visibly exposing the reading portion.

The holder includes a housing and a tray. The housing has at least first and second walls forming a cavity therebetween. One of the first and second walls has an opening or light transmissive window. The tray is received in the cavity and movable between opened and closed positions. The tray has a compartment adapted to seat and support the sampling assay device. The first opening is in registry with the reading portion when the tray is in the closed position to enable observation of the reading portion through the first opening. The light detector is connected to the housing, in registry with the first opening. The tray has a second opening extending through the compartment, which opening is in registry with the reading portion of the seated sampling device. When the tray is in the closed position, the second opening is in registry with the first opening to enable observation of the reading portion through both the first and second openings.

Not withstanding the advantages and benefits derived from the sampling device and the interface system adapted for the sampling device disclosed in the first and second copending applications, the interface system is not adapted for the luminescent (fluorescent or phosphorescent) light detection. Another potential drawback with this type of sampling device is that the chemiluminescent reaction takes place spontaneously as the chemiluminescent reagent mixes with the target analyte. In this regard, it is not possible to selectively take measurements or delay measurements once sampling is initiated. Hence, there is a need to selectively trigger luminescent reaction independently of sampling. Copending U.S. patent application Ser. No. 08/580,096, filed Dec. 22, 1995 (hereafter "third copending application"), entitled SAMPLING-ASSAY DEVICE, INTERFACE SYSTEM, AND METHOD, describes a luminescent (fluorescent or phosphorescent) assay method and device that fulfill this need. The disclosure of the third copending application, including its drawings, is incorporated herein by reference.

Specifically, the third copending application describes a sampling device, an interface for holding the sampling device, and a system and method thereof for performing an assay for a target analyte from a sample using luminescent light detection. The sampling device comprises a sampling strip housed in a container. The sampling strip has a sampling portion for receiving a sample, a reading portion for emitting light, and a transfer portion connecting the sampling and reading portions for permitting transfer of the sample from the sampling portion to the reading portion. The reading portion contains an immobilized binding agent complementary to the target analyte. This enables the reading portion to capture or immobilize the target analyte within the reading portion while allowing non-captured elements to pass through or exit the reading portion. Specifically, the binding agent preferably is an antigen complementary to the target analyte.

One or both the sampling portion and the transfer strip contains a luminescent (fluorescent or phosphorescent) labeling agent, which glows when exposed to light. The labeling agent, which preferably is chelated europium or europium compound, is contained within at least a portion of the transfer portion near or adjacent the reading portion. The labeling agent is bound to another binding agent complementary to the target analyte. Thus, the labeling agent specifically binds to the target analyte.

The container comprises a first layer and a second layer sandwiching the sampling strip and has means, which preferably is a first opening formed through the first layer and aligned with the sampling portion, to permit introduction of the sample to the sampling portion, and has a light transmissive portion exposing the reading portion. The light transmissive layer is preferably a second opening though the second layer and aligned with the reading portion. The second layer includes a light transmissive member to cover at least the second opening.

The interface comprises a sample holder, a light detector for converting light emitted from the sampling device to an output signal corresponding to the amount or intensity of the light generated, such as a photodetector or photomultiplier, connected to the holder and a light source, such as an LED, laser diode, or gas-filled lamp, connected to the holder. The holder comprises a housing having a first wall and a second wall. The first and second walls form a cavity therebetween, with the first wall having a first opening. A tray is received in the cavity and movable between an opened position and a closed position. The tray also has a compartment adapted to receive and support the sampling device and a second opening extending through the compartment. The second opening is in registry with the reading portion when the sampling device is seated in the compartment and in registry with the first openings to enable observation of the reading portion through the first and second openings.

The light detector has a light gathering window and is connected to the first wall so that the window is aligned with the first opening. The light source is aligned with the first opening and connected opposite the first opening. Specifically, the second wall has a third opening aligned with the first opening and the light source is seated in the third opening. The second wall is an enclosure having a channel and the first wall is a base plate connected to the enclosure, the channel defining the cavity.

When the tray is in the opened position, the tray blocks the first opening. The tray can also include a handle and is preferably slidable between the opened and closed positions. In this regard, the tray includes a pair of parallel slots, which are adapted to be occupied by fasteners spaced along the slots. The length of the slot less the spacing between the fasteners occupying the same slot defines the amount of the tray sliding movement. The system is adapted for use with the aforedefined sampling device and includes the aforedefined interface, and further includes a quantifier, such as an ammeter, for converting the output signal-from the light detector to quantifiable data indicative of the amount of the target analyte.

The sampling device disclosed in the first, second, and third copending applications provides a unique means for allowing light detection using known light detection devices. Because the sampling device, however, is, rather flexible, thin, and flat, it can be challenging to remove the same from the tray compartment. The sampling device needs to be removed by prying out with a fingernail or some sharp instrument. One can also turn the interface upside down and drop the sampling device. But in any event, it would be desirable to ease the sampling device removal from the tray. In addition, there is a need to protect the exposed sampling portion from cross contamination. For instance, if the interface or holder is shaken or otherwise turned sideways or upside down, it is possible for the exposed sampling portion to contact the underside of the housing upper wall, which contact could possibly introduce other samples that made contact therewith. Copending U.S. patent application Ser. No. 08/577,624, filed Dec. 22, 1995 (hereafter "fourth copending application"), entitled SAMPLING-ASSAY DEVICE, describes a sampling assay device for use with chemiluminescent and luminescent (fluorescent or phosphorescent) that fulfills this need. The disclosure of the fourth copending application, including its drawings, is incorporated herein by reference.

The fourth copending application describes a sampling device having a container and a sampling strip inside the container. The sampling strip has a sampling portion for receiving a sample, a reading portion for holding the sample with a compound that can emit light, and a transfer portion connecting the sampling and reading portions for permitting transfer of the sample from the sampling portion to the reading portion. The container has means to permit introduction of the sample to the sampling portion and a light transmissive portion exposing the reading portion. A shield extends from the container adjacent the exposed sampling portion. The shield has a portion extending beyond one end of the container and is movable to and from the sampling portion and can be wrapped around the one end.

Specifically, the container comprises a first layer and a second layer sandwiching the sampling strip. The shield is attached to or integral with the first layer and has means for permitting the extending portion to wrap around the one end of the container. The wrap around means is preferably a preformed fold or crease, or even a perforation. A tab or handle is attached to or formed integrally with the first layer. Alternatively, the tab can also be attached to or integral with the shield.

The sample introducing means preferably is a first opening formed through the first layer and aligned with the sampling portion. Similarly, the light transmissive layer is preferably a second opening though the second layer and aligned with the reading portion. The second layer preferably also includes a light transmissive member to cover at least the second opening.

According to one embodiment, the sampling strip is composed of an adsorbent material. In another embodiment, the sampling strip includes a poly-carbonate membrane that is light transmissive.

The sampling device can further include a sample collecting member, which preferably is adsorbent, in contact with the sampling portion inside the container and aligned with the first opening. The sample collecting member receives the sample and transfers the sample to the sampling portion.

According to one embodiment, the compound is a reagent, preferably an enzyme in a dried state, contained within the reading portion. When the reagent is mixed with the analyte, it produces chemiluminescent light. More preferably, the reagent is luciferase-luciferin in a dried state.

According to another embodiment, the compound, which preferably is a luminescent labeling agent (phosphorescent or fluorescent) with a binding agent for tagging the analyte, is contained within at least a portion of the transfer portion. The labeling agent glows when it is exposed to light. Preferably, the labeling agent is chelated europium or europium compound. The reading portion contains an immobilized binding agent, such as an antigen, specific to the analyte, for capturing the labeled analyte within the reading portion. In this embodiment, the sampling strip further includes a collecting portion contiguous with the reading portion. This collection portion is designed to absorbs any excess liquid containing the labeling compound not coupled to the binding agent. Accordingly, as the analyte immobilized in the reading portion carries the labeling agent that glows when exposed to light, the amount of light produced after exposure to light correlates to the amount of analyte present in the sample. In operation, as the sample contained in liquid travels across the transfer portion, the target analyte will pickup the labeling agent. Other organisms mixed with the labeling compound and the excess labeling compound, however, are not specific to the binding agent. Thus, they will not be captured in the reading portion, but rather will flow through. The target analyte, however, since it is specific to the binding agent, will be captured and remain in the reading portion.

The sampling device according to the fourth copending application is particularly adapted for use with a sampling-device holding interface, which has a housing and a tray for seating the sampling device, as described in the second and third copending applications. The housing has a cavity for accepting the tray with the sampling device. The cavity is light-light tight when the tray is closed. The housing is connected to a light detector or the like to measure the amount of light generated by the sample. The housing can have also have a light source for triggering reaction of the luminescent labeling agent.

SUMMARY

The present invention relates to a disposable integral sample assay device and a holder.

DETAILED DESCRIPTION OF THE DRAWINGS

Figure 1:
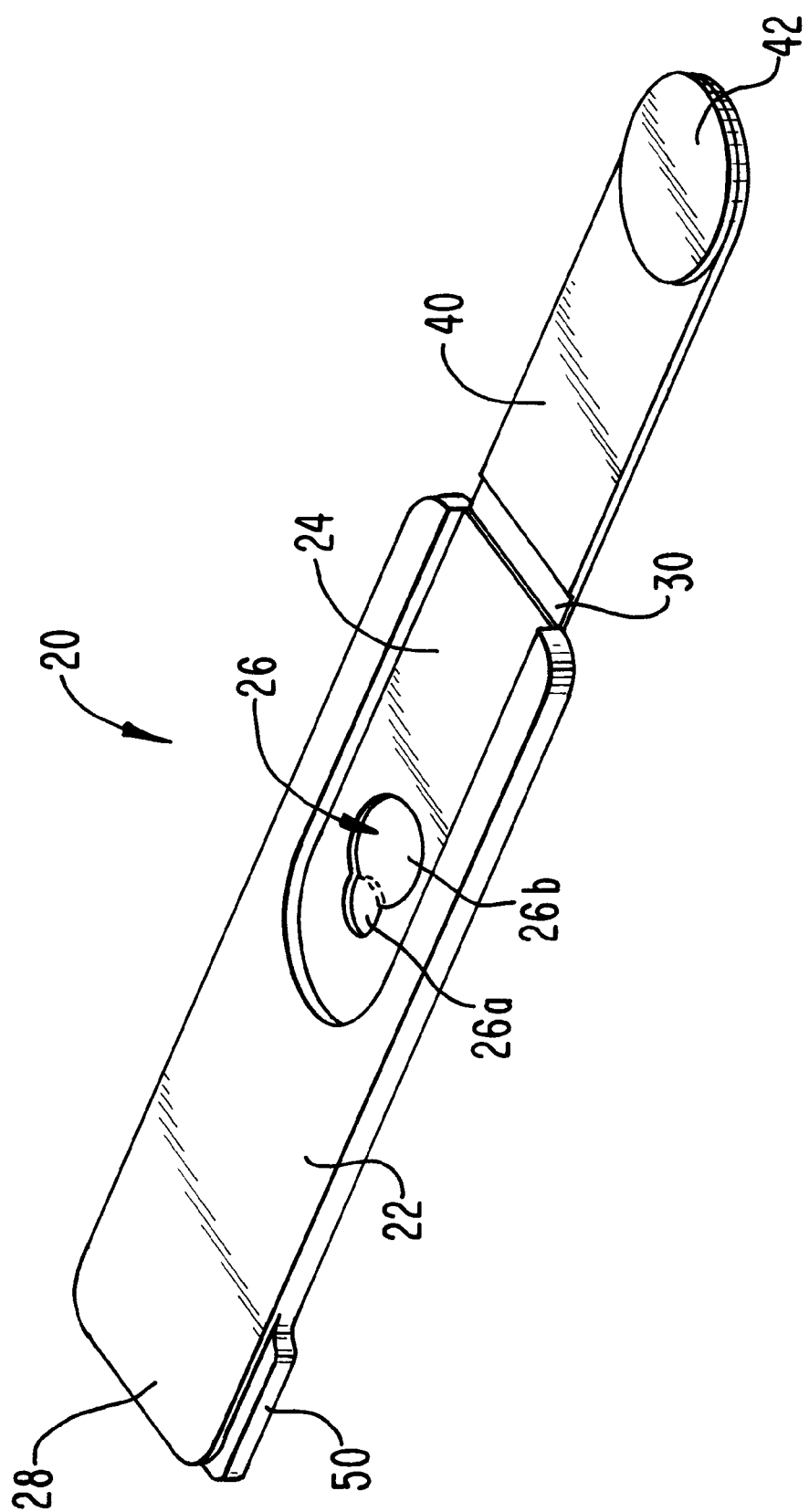
FIG. 1 is a perspective view of a sampling assay device and holder according to the present invention.

FIG. 1 illustrates a combined sampling assay device and a holder 20 (hereafter "assay device") presently contemplated for use with the interface or the sampling-device holder disclosed in the second and third copending applications, the disclosures of which, including their drawings, are incorporated herein by reference. The present assay device 20, which is disposable, replaces the sliding tray and the sampling device described in the second and third copending applications.

Specifically, the present assay device 20 comprises a generally flat plate-like body 22, preferably of plastic material, and a collection arm 40, also preferably of plastic material, one end of which is connected, preferably pivotally or foldably, to one end of the body 22. The collection arm 40 can be integrally formed with the body 22.

The flat body 22 has a blind-recess, first recess, or well 24 (having a bottom) forming a compartment for flatly supporting and seating the collection arm. The height or depth of the well 24 is preferably greater than the thickest portion of the arm 40 to maintain the arm inside within the well 24. Preferably, a hinge 30 is formed at the juncture of the arm 40 and the body 22, which hinge allows the arm to move, for example fold or pivot, so that the arm occupies or is positioned within the well 24. Alternatively, the hinge 30 is frangible to allow for removal of the arm 40 from the body 22, and then insertion of the arm 40 into the well 24. In any case, the arm is dimensioned so that it is frictionally maintained in place within well 24.

The well has a pear-shaped opening or recess 26, a second recess, occupied by an adsorbent material, which may be fibrous, such as glass fiber, cotton, dacron, or paper and the like, and it may be porous, such as porous polyethylene or sintered glass and the like. The opening or recess 26 includes a transport section 26a (smaller area) and a reading portion 26b (larger area) both occupied by the adsorbent material. If an opening is provided, a light transparent layer is preferably provided underneath the opening to prevent the sample from leaking but provide light transmission. Alternatively, if a recess is provided, the bottom wall needs to be light transmissive, either clear or translucent so that light intensity can be measured from the bottom of the device.

In the second and third copending applications, the tray slides into to the light intensity measuring interface with a light-tight fitting. Similarly, the present assay device can slide into the interface. In essence, the present invention is an improvement over the prior interface or sample assay holding device. That is, the present assay device integrally incorporates the tray and the sample assay device. Similarly, the assay device has a handle portion 28 at the end opposite the one end where the collecting arm is connected or formed. When the present assay device is inserted into the interface, the handle portion 28 protrudes so that it can be grasped and pulled. Also to prevent improper insertion, at least one of the sides of the handle portion 28 can be provided with a key 50. Of course, the interface or the holding device would require a key slot.

Similar to the sampling assay device disclosed in the first, second, third, and fourth copending applications, the collection arm has a sampling collecting portion comprising collection pad 42, preferably adsorbent, preferably composed of fibrous material, such as glass fiber, cotton, dacron, or paper, and it may be porous, such as porous polyethylene or sintered glass. Similarly, the transport portion 26a can have a similar adsorbent pad.

The reading portion 26b, where the chemiluminescent reaction is designed to occur, contains one or more chemiluminescent reagents, preferably in a dried form. Additionally, the reading portion can contain other reagents useful for the assay including, for example, the detergent or other bacteriolytic reagent for extracting ATP from bacteria.

A wide variety of chemiluminescent chemistries can be used with the present sampling assay device. Acceptable chemiluminescence chemistries include, among others, the reaction of hydrogen peroxide with horseradish peroxidase labelled antibodies and luminol, enhanced horseradish peroxidase, reactions that include the use of diacylhydrazides, acridinium salts, dioxitanes, and bioluminescent reactions involving cofactors, such as reduced nicotine adenine dinucleotide in the case of marine bacteria. A particularly preferred chemiluminescent chemistry is the firefly ATP assay, which utilizes luciferase and at least one cofactor to generate light from ATP.

When preparing the reading portion, reagents may be conveniently applied as a solution and then dried or they may be applied in a dry form, such as a powder or suspension in an organic solvent or slurry. Other methods are known in the art and the preferred one can be determined by characteristics of the reaction components desired.

In operation, the sample collecting portion is exposed to the target area, for instance, by contacting or swabbing the suspected surface, liquid, or other area suspected of containing the sample with the collection pad 42. Alternatively, the sample to be tested can be directly introduced to the collection pad 42. As described in the copending applications, carrier liquid is introduced to the member, if needed, to wet the target analyte and move, by lateral flow any analyte present to the reading portion where one or more dried chemiluminescent reagents are present. To move the sample to the reading portion, the collecting arm 40 is folded over so that the transport portion 26a is exposed to the collection pad 42. The collecting arm is maintained in the closed position thereafter, preventing cross-contamination, as described in the fourth copending application. If the target analyte to be tested is in a liquid form, then the carrier liquid may not be necessary.

The carrier liquid preferably includes a bacteriolytic agent that releases ATP from any bacteria present in the sampling portion. Acceptable carrier liquids include, among others, a buffer solution or a buffer solution with detergent. Buffer solutions of TRIS, HEPES buffers at pH 7.0 to 9.0, and most preferably HEPES buffer at 7.8 with EDTA are preferred when used with firefly luciferase from *Photinus pyralis*. EDTA is a preferred ingredient because ATP degrading enzymes require divalent metal cations for activity and EDTA chelates these. Detergent, which can also be present in the sampling or reading portion or included with the carrier, dissolves in liquid added to the sampling device and serves to open cells and liberate cell components. Several suitable detergents or combination of detergents are known to those skilled in the art and include, nonionic detergents such as Triton X-100, Nonidet P40, n-Undecyl Beta-D glucopyranoside, Zwitterionic detergents such as n-hexadecyl-N,N-dimethyl-3-ammonio-1-propanesulfonate, and cationic detergents such as alkyltrimethylammonium bromides, benzalkonium chloride, cetyldimethyl-ethylammonium bromide, dodecyltrimethylammonium bromide, and cetyltrimethylammonium bromide. The concentration of detergent solution varies for each type of detergent and can range from 0.1% to 6%, and preferably from 0.5% to 2.0%.

Any analyte present in the transport portion 26a is moved to the reading portion 26b by lateral flow or wicking action or diffusion, etc. The analyte along with any carrier liquid reaching the reading portion rehydrates the dried chemiluminescent reagent contained in the reading portion. Any ATP present in the carrier liquid reacts with the rehydrated chemiluminescent reagent present in the reading portion to emit light. The degree of chemiluminescence light produced in response to the presence of target analyte in the sample can be detected using the interface described in the second copending application, where the degree correlates to the amount of the analyte present.

A target analyte as used herein, is a molecule such as a protein, cell metabolite or microorganism such as a prokaryotic cell, virus, microplasma or free living eukaryotic cell. The target analyte can be introduced by physical contact such as by swabbing a suspected contaminated surface with the device or by introducing the sample in liquid form by, for example, an eye dropper or other dispenser, or by brief immersion of the device in the liquid to be tested.

Once the sampling has been made, the assay device 20 is slid into the interface described in the second application, for example, where the reading portion 26b will be in registry with the light reading opening.

Given the disclosure of the present invention, one versed in the art would readily appreciate that there may be other embodiments and modifications well within the scope and spirit of the present invention. Accordingly, all expedient modifications readily attainable by one versed in the art from the present disclosure within the scope and spirit of the present invention are to be included as further embodiments of the present invention.

What is claimed is:

1. An integrated sample assay device and a holder, comprising:
    a flat body having a first recess and a second recess formed within the first recess, the second recess having a transport portion and a reading portion being light transmissive and containing a reagent; and
    a collecting arm having a sampling collecting portion, one end of the collecting arm being connected to the flat body;
    wherein the collecting arm is positionable within the first recess to expose the sampling collecting portion to the transport portion.

2. An integrated sample assay device and holder as described in claim 1, wherein the sampling collection portion of the collecting arm contacts the transport portion but does not contact the reading portion.

3. An integrated sample assay device and holder as described in claim 1, wherein the first recess of the flat body forms a compartment that is sized to maintain the collecting arm inside the well.

4. An integrated sample assay device and holder as described in claim 3, wherein the collecting arm is dimensioned so that it frictionally fits within the first recess.

5. An integrated sample assay device and holder as described in claim 3, wherein the depth of the first recess is greater than the thickest portion of the collecting arm.

6. An integrated sample assay device and holder as described in claim 1, wherein the transport portion is smaller than the reading portion.

7. An integrated sample assay device and holder as described in claim 1, further comprising a handle portion at one end opposite the end where the collecting arm is connected to the flat body.

8. An integrated sample assay device and holder as described in claim 7, further comprising a key to prevent improper insertion of the device into a light intensity measuring interface.

9. An integrated sample assay device and holder as described in claim 1, further comprising a reagent for a chemiluminescent reaction.

10. An integrated sample assay device and holder as described in claim 9, wherein the chemiluminescent reaction is selected from the group consisting of reaction of hydrogen peroxide with horseradish peroxidase, enhanced horseradish peroxidase, reaction that includes the use of a diacylhydrazide, reaction that includes the use of an acridinium salt, reaction that includes the use of a dioxitane, and a bioluminescent reaction involving a cofactor.

11. An integrated sample assay device and holder as described in claim 1, wherein the sample assay device further includes a collecting portion contiguous with the reading portion.

12. An integrated sample assay device and holder as described in claim 11, wherein the reading portion contains an immobilized binding agent.

13. An integrated sample assay device and holder as described in claim 12, wherein the immobilized binding agent is an antigen.

* * * * *